United States Patent
Armbruster et al.

(10) Patent No.: US 11,714,082 B2
(45) Date of Patent: Aug. 1, 2023

(54) METHOD FOR DETERMINATION OF MEMBERS OF THE S100 FAMILY OF CALCIUM BINDING PROTEINS BY IMMUNOTURBIDIMETRY

(71) Applicants: Immundiagnostik AG, Bensheim (DE); Diasys Diagnostic Systems GmbH, Holzheim (DE)

(72) Inventors: Franz-Paul Armbruster, Bobenheim-Roxheim (DE); Matthias Grimmler, Elz (DE); Pia Schu, Schmelz (DE); Tobias Becker, Elz (DE); Felix Walzer, Seeheim (DE)

(73) Assignees: Immundiagnostik AG, Bensheim (DE); DiaSys Diagnostic Systems GmbH, Holzheim (DE)

( * ) Notice: Subject to any disclaimer, the term of this patent is extended or adjusted under 35 U.S.C. 154(b) by 601 days.

(21) Appl. No.: 16/611,942

(22) PCT Filed: May 9, 2018

(86) PCT No.: PCT/EP2018/062159
§ 371 (c)(1),
(2) Date: Nov. 8, 2019

(87) PCT Pub. No.: WO2018/206737
PCT Pub. Date: Nov. 15, 2018

(65) Prior Publication Data
US 2021/0382044 A1 Dec. 9, 2021

(30) Foreign Application Priority Data
May 9, 2017 (EP) .................... 17170291

(51) Int. Cl.
*G01N 33/543* (2006.01)
*G01N 33/545* (2006.01)
*G01N 33/68* (2006.01)

(52) U.S. Cl.
CPC ..... *G01N 33/54346* (2013.01); *G01N 33/545* (2013.01); *G01N 33/68* (2013.01); *G01N 2333/4727* (2013.01)

(58) Field of Classification Search
CPC ........... G01N 33/54346; G01N 33/545; G01N 33/68; G01N 2333/4727; G01N 33/54313
See application file for complete search history.

(56) References Cited

U.S. PATENT DOCUMENTS

2005/0176063 A1* 8/2005 Kamei ............... G01N 33/5306
435/7.1
2008/0299558 A1* 12/2008 Kondo ................. C12Q 1/6816
435/6.12

FOREIGN PATENT DOCUMENTS

EP 0 038 181 A2 10/1981
WO WO 2004/057341 A2 7/2004

OTHER PUBLICATIONS

T. Nilsen et al., "A Novel Turbidimetric Immunoassay for Fecal Calprotectin Optimized for Routine Chemistry Analyzers," Journal of Clinical Laboratory Analysis, vol. 31, No. 4, pp. e22061, Sep. 15, 2016.
T. Nilsen et al., "A New Turbidimetric Immunoassay for Serum Calprotectin for Fully Automatized Clinical Analyzers," Journal of Inflammation, vol. 12, No. 1, pp. 45, Jul. 25, 2015.
"Bühlmann fCAL® Turbo Calprotectin Turbidimetric Assay for Professional Use: Reagent Kit." pp. 1-6, Feb. 24, 2017, URL:https://www.buhlmannlabs.ch/wp-content/uploads/2015/06/20170224-KK-CAL_IFU-CE-Reagent.pdf.
"Bühlmann fCAL® Turbo Calprotectin Turbidimetric Assay for Professional Use: Calibrator Kit" pp. 1-3, Jun. 29, 2016. URL:https://www.buhlmannlabs.ch/wp-content/uploads/2015/06/160629-KK-CAL_IFU-CE-_Calibrator.pdf.
M-H. Aleksandra et al., "Turbidimetric Determination of Fecal Calprotectin Using Two Table Top Chemistry Analyzers: Mindray BS-200E and Cobas c111." Clinical Laboratory, vol. 63, No. 5, pp. 907-913, May 1, 2017.

* cited by examiner

*Primary Examiner* — Shafiqul Haq
*Assistant Examiner* — Nam P Nguyen
(74) *Attorney, Agent, or Firm* — Blank Rome LLP

(57) ABSTRACT

A method for measuring the presence of calprotectin (S100A8/A) heterodimer in a biological sample using a particle-enhanced turbidimetric immunoassay (PETIA) based on monoclonal antibodies. The method can be adapted on automated standard analyzers and provides a reliable clinical measurement of calprotectin in faecal samples and extracts. The method is comparable to commerical two-site sandwich ELISA. The disclosed method counters spontaneous agglutination caused by calcium ions and low-molecular weight calcium-binding S100 proteins as observed with conventional PETIAs. The method can be used for measuring the presence of human calprotectin in stool, urine, serum, plasma, synovial liquid and other body liquids. Metrological traceability and high commutability with conventional immunoassays (ELISA) has been shown despite of different measurement principles used.

10 Claims, 6 Drawing Sheets

METHOD FOR DETERMINATION OF MEMBERS OF THE S100 FAMILY OF CALCIUM BINDING PROTEINS BY IMMUNOTURBIDIMETRY

FIELD OF THE DISCLOSURE

The present application relates to a turbidimetric method and a test system for quantitative determination of members of the S100 family of calcium-binding proteins in bodily fluids and faeces. The test kit comprises antibodies, buffers and a kit of parts for use in the diagnosis of acute and chronic inflammatory diseases and conditions.

TECHNICAL BACKGROUND

The term calprotectin encompasses two granulocyte proteins with relative molecular weights of 36500 Daltons and isoelectric points at pH 6.3 and 6.5 (U.S. Pat. No. 4,833,074; Fagerhol et al., Scand. J. Haematol. 24, 393-398 (1980). Fagerhol et al., Bull. Europ. Physiopath. Resp. 16 (suppl), 273-281 (1980). Alternative names include low-molecular weight S100A8 and S100A9 calcium-binding proteins, myeloid related protein 8 (MRP8), myeloid related protein 14 (MRP14), migration inhibitory factor-related proteins 8/14 (MRP8-MRP14), S100a/b, calgranulin A/B, cystic fibrosis antigen (CFA), human leukocyte protein, leukocyte L1-protein complex, 6088 antigen, and 27E10 antigen. Calprotectin is a proven marker for neutrophil activation as its concentration in bodily fluids and matrices is indicative for the turnover of leukocytes and their infiltration in tissues. It has therefore become a widely used biomarker in clinical chemistry for infections, acute and chronic inflammatory disorders and other diseases. The measurement of calprotectin can be used for distinguishing bacterial infections from other causes as well as for diagnosis of non-infectious systemic inflammation (Striz, I & Trebichaysky, Calprotectin—a pleiotropic molecule in acute and chronic inflammation, Physiological research/Academia Scientiarum Bohemoslovaca (2004) 53(3): 245-53; Nilsen T et al, *A new turbidimetric immunoassay for serum calprotectin for fully automatized clinical analysers*, Journal of Inflammation (2015) 12:45; Johne B et al, *Functional and clinical aspects of the myelomonocyte protein calprotectin*, Mol. Pathol. 1997; 50:113-23; Nielsen T et al, *Serum calprotectin levels in elderly males and females without bacterial or viral infections*, Clin. Biochem 2014; 47(12):1065-8). Calprotectin has further been proposed a marker of the potential for a cardiovascular disease (CVD) before the onset of CVD symptoms in symptom-free subjects (cf. EP 1 573 335 B1).

The simultaneous presence of different S100 mono- and multimers in addition to the heterodimer however complicates the immunological determination of calprotectin in biological samples (blood, serum, synovial fluids, etc.) and matrices (feces). The $Ca^{2+}$ and $Zn^{2+}$-binding properties of the S100A8/A9 proteins have further a pivotal influence on their conformation and oligomerization. S100A8 and S100A9 tend to form tetramers in the presence of calcium or zinc ions whereas the heterodimer seems to be the prevalent form in the absence of calcium (cf. Grabarek Z, *Structural basis for diversity of the EF-hand calcium-binding proteins*, J Mol Biol (2006), 359: 509-25). The mixing of purified S100A8 and S100A9 does not automatically produce a calprotectin with properties as the heterodimer secreted by granulocytes. Experiments with mutated S100A8 and S100A9 suggest that the homo- and hetero oligomerization of S100A8 and S100A9 is also functionally and diagnostically relevant.

Calprotectin is expressed in vivo during various stages of myeloid differentiation, in circulating neutrophils and monocytes, while absent in normal tissue macrophages and lymphocytes, and up-regulated in many types of cancer, including gastric, esophageal, colon, pancreatic, bladder, ovarian, thyroid, breast and skin cancers, neurodegenerative disorders as well as in inflammatory and autoimmune diseases and pathologies. Chronic inflammatory conditions such as psoriasis lead to an expression in the epidermis. Calprotectin is found in high concentrations at local sites of inflammation as well as in serum (blood) and feces of patients with inflammatory diseases, rheumatoid arthritis, cystic fibrosis, inflammatory bowel disease, Crohn's disease, giant cell arteritis, Sjögren's syndrome, systemic lupus erythematosus, and progressive systemic sclerosis. Calprotectin is also involved in the formation and deposition of amyloids in the aging prostate known as corpora amylacea inclusions.

Numerous roles have been ascribed to calprotectin. It can induce neutrophil chemotaxis and increase bactericidal activity by promoting phagocytosis and/or a degranulation of neutrophils by a MAPK-dependent mechanism (Simard J. C. et al, *Induction of neutrophil degranulation by S100A9 via a MAPK-dependent mechanism*, J Leukoc Biol. (2010) 87(5):905-14). Antimicrobial, oxidant-scavenging and apoptosis-inducing activities as well as proinflammatory activities (e.g. recruitment of leukocytes) have further been ascribed to calprotectin which seems to be an amplifier of inflammation in autoimmunity as well as a stimulant of innate immune cells via its binding to pattern recognition receptors such as Toll-like receptor 4 (TLR4) and the receptor for advanced glycation end-products (AGER). Other activities include the promotion of cytokine and chemokine production and regulation of leukocyte adhesion and migration. The binding to TLR4 and AGER activates the MAP-kinase and NF-kappa-B signaling pathways which results in the amplification of the proinflammatory cascade. The antimicrobial activities towards bacteria and fungi likely result from the binding of $Zn^{2+}$ and $Mn^{2+}$ ions which are essential for microbial growth. Transnitrosylase activity has also been found for calprotectin and the iNOS-S100A8/A9 transnitrosylase complex has been proposed to direct selective inflammatory stimulus-dependent S-nitrosylation of targets comprising a [IL]-x-C-x-x-[DE] motif. Calprotectin can further act as an alarmin or danger associated molecular pattern (DAMP) molecule.

The true and precise measurement of calprotectin in biological samples and matrices is essential if results are to be interpreted for diagnostic purposes and patient care, notably for monitoring the treatment of acute and chronic inflammatory disorders with biologicals. In particular, results must be comparable if common diagnostic decision values and clinical research findings are to be applied. The metrological problem in view of the variable oligomerization states of calprotectin can be broken into traceability of measured values, measurement uncertainty and commutability. When traceability is not achieved result comparability must be realized by other methods since measurements are the core activity of clinical laboratories. The goal is that patients' results are traceable to the highest available reference to improve the quality of diagnostic results.

Conventional methods for measuring calprotectin use polyclonal antibodies, either in free form or bound to a solid phase (cf. WO2012/175616, WO2013/132347, WO2014/037588, US20170108507). The parallel determination by an immunoassay (e.g. by an enzyme-linked immuno sorbent assay—ELISA) or of purified calprotectin in spiked sample solutions using UV/VIS, Biuret, Bradford or Coomassie Blue gives however no conclusive answers to the standard problem since calprotectin can take the form of dimers (S100A8/A9), (S100A8/A9)$_2$ tetramers or even oligomers (T. Vogl et al, Poster: *Towards a Reference Material for the Standardization of Calprotectin* (S100A8/Ag; MRP8/14) Immunoassay, presented at FOCUS (Association for Clinical Biochemistry and Laboratory Medicine), May 3-5, 2017, Leeds, UK). The use of mutated S100A8 and S100A9 proteins having at least one mutation in the high- or low-affinity calcium binding region has been suggested as those recombinant proteins can no longer oligomerize (WO 2016/116881).

Turbidimetric immunoassays provide the advantages of easy procedures and an automated analyzer. In the particle-enhanced turbidimetric immunoassay (PETIA) the target-specific antibodies are bound to particles ("sensitized particles") so that the antibody-antigen reaction results in an agglutination of particles which can be measured by spectrometry (cf. EP 0 061 857; EP1 205 755 B1; and references therein). One type of particulate reagent is sufficient when the target antigen is recognized by two or more antibodies, bridging two or more latex particles (Methods in Enzymology (1981) 74, 106-139, Academic Press, New York; EP 1 739 430 B1; EP1 573 335 B1). Unspecific reactions between the particulate reagent and the sample may also lead to an agglutination and increased turbidity (cf. JP 11 023 573 A, JP 58 144 748 A, EP 1 205 755 B1). Safe and complete inhibition of unspecific reactions represent in particular a problem if polyclonal antibodies are used bound to the particulate reagent or the target is extracted from a complex or variegated matrix like feces (cf. EP 0 038 181 B1). A standard with mutated calprotectin (mutS100A8/A9) is of little use when measuring the presence of endogenous calprotectin in human matrices and samples, e.g. those obtained from the respective patients, or by an agglutination method. Currently, calprotectin is determined in biological samples employing a particle-enhanced turbidimetric immunoassay (PETIA) wherein immobilized polyclonal antibodies bind to multiple epitopes on calprotectin so that any type of S100 protein may lead to agglutination, regardless whether it is in the oligomerization state secreted by granulocytes or not. This causes non-diagnostic cut-off values, measurement uncertainty and undermines commutability, in particular as polyclonal antisera are prone to produce to unspecific agglutination.

The observed spread in the method comparison between an ELISA based on monoclonal antibodies and a PETIA based on an agglutination employing polyclonal antibodies as well as the non-commutability of diagnostic cut-off values are further causes for concerns. While monoclonal antibodies are easier to standardize and allow quality control to a defined standard over the entire product life-time, there is the combined problem of obtaining an agglutination reaction, measurement sensitivity and specificity for calprotectin as secreted by granulocytes. The state of the art in the determination of calprotectin in biological samples and matrices therefore represents a problem.

SUMMARY OF THE INVENTION

A solution to these problems is achieved by an in vitro method as described in claim 1. Preferred embodiments of the method have been defined in the dependent claims 1 to 14. Another aspect of the invention relates to a kit, e.g. for use in a turbidmetric or nephelometric immunoassay, comprising two reaction-components as defined in claim 15.

Accordingly, it is one objective to provide an in vitro method of measuring the presence of calprotectin in a biological sample of a patient, comprising the steps of comprising the steps of: a) collecting a predetermined amount of said biological sample; b) solubilizing and extracting said biological sample in a pre-determined amount of aqueous organic buffer having i) a pH between 5.0 and 6.0, ii) an osmolality of at least 150 mosmol/kg of H$_2$O, iii) 0.01 to 0.1% percent by weight anionic surfactant, iv) wherein the organic buffer molecules can coordinate with calcium and zinc ions, and iv) and, optionally, homogenizing and extracting the matrix of said biological sample followed by a removal of any particulate material to obtain a sample solution with a defined solubilized presence of calprotectin (S100A8/A9) as secreted by granulocytes (with intact lysosomal compartments); c) mixing a defined amount of said sample solution of step (b) with an amount of reagent to obtain a mixture comprising nanoparticles having immobilized monoclonal antibodies or fragments thereof which specifically bind either one of S100A8 and S100A9 or calprotectin (S100A8/A9) and a particle-bound antibody-antigen reaction with calprotectin (S100A8/A9); d) incubating the mixture of step c) for an interval of time; and e) acquiring an optical property of the mixture and determining a signal indicative of the content of calprotectin (S100A8/A9) based on the optical property of the mixture; f) relating said content to a calibrated control and assessing the clinical condition of said patient based on the measured presence of calprotectin (S100A8/A9) in said biological sample. If the calprotectin is determined as described above, the amount is metrologically traceable to a measurement of a calprotectin standard isolated from granulocytes with intact lysosomal compartments. The initial methods for determination of calprotectin used polyclonal monospecific antibodies as the structure, number and concentration of the calcium-binding proteins of the S100 family varied.

The step of acquiring an optical property comprises determining an absorbance, transmittance, reflectance, light scatter, fluorescence, or scintillation value. Turbidimetric or nephelometric measurements are preferred, and most preferred is a particle-enhanced turbidimetric immunoassay (PETIA) wherein steps b) and c) comprise the use of two reagent-components.

The nanoparticles have preferably diameters from 150 to 350 nm for increased sensitivity. More preferred is a PETIA, wherein the antibodies are bound to two types of particles having homogenous diameters in the range from i) 150 to 200 nm and ii) from 250 to 350 nm for increased measurement range. Said nanoparticles may be made up of carboxylated polystyrene or chloromethyl-activated polystyrene.

The particle-bound antibody-antigen reaction is preferably performed in a mixture having a pH between 5.0 and 6.0 and comprising an anionic surfactant or sodium dodecylsulfate and Ca$^{2+}$-coordinated buffer molecules.

The biological sample may be faeces or, more precisely, an extract of faeces, as the determination of faecal calprotectin has become an integral component of the laboratory work-up of inflammatory bowel disease. The monitoring of an inflammation parameter in the stool and of a marker for neutrophilic granulocyte activity such as calprotectin facilitates early recognition of a recurrent disease flare following established remission. Other preferred biological sample are blood, serum or plasma and urine, e.g. for diagnosis and differentiation of pre- and intrarenal kidney disease, or other inflammatory diseases of the cardiovascular system.

The buffer composition is preferably made up of at least one salt selected from the group comprising polycarboxylic acids, tricarboxylic acids, aconitic acids, tricarballylic acids, dicarboxylic acids, oxalic acid, malonic acid, succinic acid, glutaric acid, adipinic acid, pimelinic acid, alpha-, beta-, and gamma-hydroxy carboxylic acids, hydroxy dicarboxylic acids, malic acid, citric acid, tartratic acids, malonic acid, gluconic acid, 5-ketogluconic acid, 2-ketogluconic acid, dihydroxy maleic acid, maleic acid, fumaric acid, nitrilotriacetic acid, lactic acid, and/or ascorbic acid. The calcium sequestering buffer of step b) comprises preferably at least one salt of citrate, acetate or maleate, protease-treated serum albumin, and 0.01 to 0.1 percent by weight of anionic surfactants. The addition or presence of unspecific IgM antiserum in the reaction-components may be necessary for initiation and acceleration of the agglutionatin reaction.

It is another objective to provide a test kit for measuring the presence of calprotectin in a biological sample by a particle-enhanced turbidimetric immunoassay as described. The test kit may comprise a first reagent-component comprising
- 20 to 1000 mmol/L organic buffer with a pH in the range from 5.0 to 6.0;
- 50 to 300 mmol/L salt of sodium, potassium or lithium;
- 0.1 to 1.5% protease-treated serum albumin;
- 0.01 to 0.1% (w/v) sodium dodecyl sulfate, and
  - optionally beta-aldoses, triose, tetroses, pentoses, hexoses, glucan, dextran and/or sugar to achieve an osmolality of at least 200 mmosM/L; and
- a second reagent-component comprising
  - 0.01 to 0.5% (w/v) latex particles of 150 to 350 nm diameter carrying immobilized monoclonal antibodies which bind either one of S100A8 and S100A9 or calprotectin (S100A8/A9).

The buffer reagents in said reaction-components for sequestering calcium and zinc ions may comprise at least one salt of an organic acid selected from the group consisting of polycarboxylic acids, tricarboxylic acids, aconitic acids, tricarballylic acids, dicarboxylic acids, oxalic acid, malonic acid, succinic acid, glutaric acid, adipinic acid, pimelinic acid, alpha-, beta, and gamma-hydroxy carboxylic acids, hydroxy dicarboxylic acids, malic acid, citric acid, tartratic acids, malonic acid, gluconic acid, 5-ketogluconic acid, 2-ketogluconic acid, dihydroxy maleic acid, maleic acid, fumaric acid, nitrilotriacetic acid, lactic acid, ascorbic acid. Such organic acids can co-ordinate in water with calcium and zinc ions, in particular when used in combination.

While not wishing to be bound by any theory, the acidic pH of 5.0 and 6.0 and the calcium ion coordination of the buffer reagents seem to create conditions specific for the calprotectin as present in neutrophilic granulocytes, which S100A8 and S100A9 proteins have a pKI of 6.3 and 6.5 and are strongly binding calcium by bidentate, unidentate, and pseudo-bridging. The presence of a small amount of anionic surfactant such as sodium dodecyl sulfate may be needed to keep the proteins in solution while not inhibiting the reaction between the particle-bound antibodies and the target. The buffer composition as claimed is in terms of pH and osmolality similar to the cellular millieu wherein calprotectin is present in the granulocytes. Granulocyte have an internal pH between 5.0 and 6.0 and a calcium ion concentration 100 to 1000 times below the environment.

A preferred aspect of the disclosure consists in a kit with two reaction-components supporting a determination by turbidimetry. This may be a particle-enhanced turbidimetric immunoassay (PETIA) comprising two reagent-components in support of steps b) and c). A most preferred embodiment relates to a determination of faecal calprotectin together with a device for transfer of a defined amount of faeces into a buffer for dilution and extraction of calprotectin from a stool matrix, e.g. as disclosed in DE10 2012 109 457 B4, DE10 2008 057 866 B4 U.S. Pat. No. 5,246,669 A, JP-H10-300 642 A, DE10 2007 07 760 B3.

Further objectives, features and advantages will become apparent from a consideration of the drawings and ensuing description of representative examples which are for illustration only and not limiting, as a person skilled in the art will also consider potential modifications thereof. The scope of the disclosure has been defined in the claims.

DETAILED DESCRIPTION OF THE INVENTION

Figure 1:
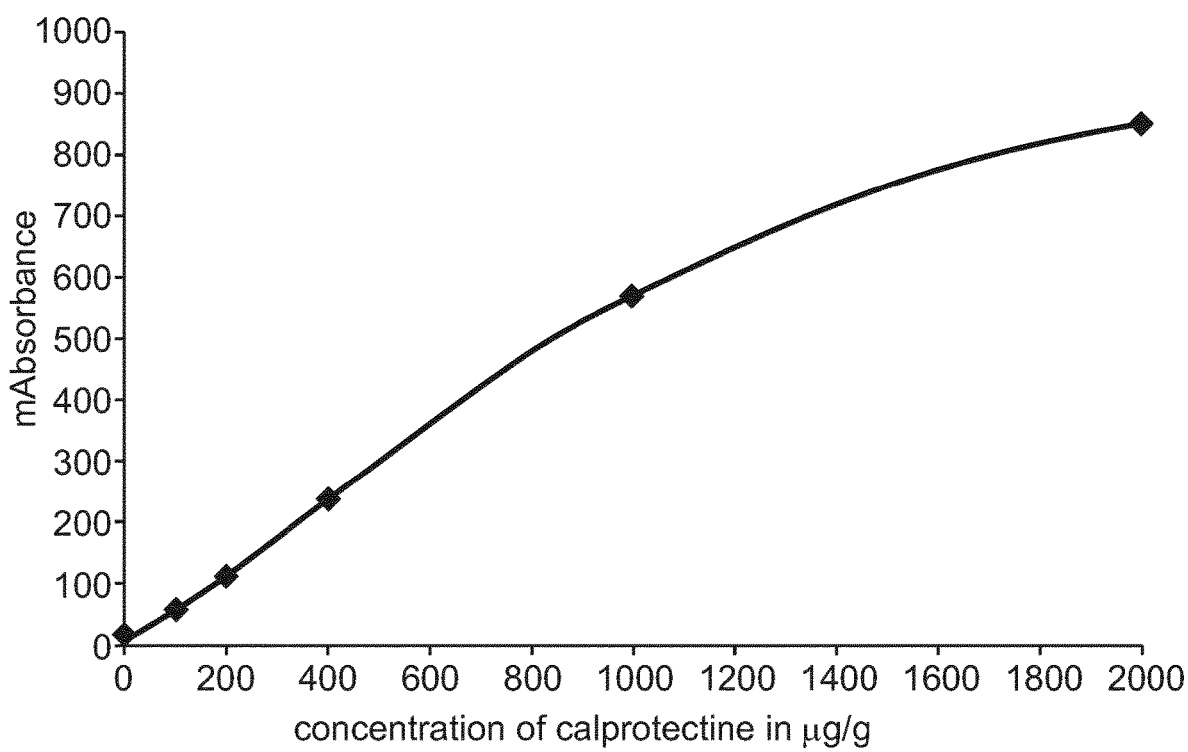
FIG. 1 is a diagram with a calibration curve of a turbidimetric immunoassay employing a monoclonal mouse anti-calprotectin (S100 A8/A9) antibody covalently bound to latex particles having a diameter of 180 nm.

In the past, it has been difficult to establish a specific diagnostic threshold of calprotectin in faeces, and pronounced inter-assay differences exist between different commercial assays due to the different extraction methods and buffers (Sipponen T, Kolho K L. *Faecal calprotectin in children with clinically quiescent inflammatory bowel disease*. Scand J Gastroenterol. 2010, 45:872-877; Gisbert J P, Bermejo F, Perez-Calle J L, et al. *Fecal calprotectin and lactoferrin for the prediction of inflammatory bowel disease relapse*. Inflamm Bowel Dis. 2009, 15:1190-1198; Walkiewicz D, Werlin S L, Fish D, et al. *Fecal calprotectin is useful in predicting disease relapse in pediatric inflammatory bowel disease*. Inflamm Bowel Dis. 2008, 14: 669-673; D'Inca R, Dal Pont E, Di Leo V, et al. *Can calprotectin predict relapse risk in inflammatory bowel disease?* Am J Gastroenterol. 2008 103:2007-2014 Tibble J A, Sigthorsson G, Bridger S, et al. *Surrogate markers of intestinal inflammation are predictive of relapse in patients with inflammatory bowel disease*. Gastroenterology. 2000; 119:15-22). The described method provides the advantage that extraction and measurement buffers provide a environment similar to the one found when destroying granulocytes but keeping intact lysosomal membranes and acidic compartments. In other words, the environment is physiological similar to the one into which granulocytes set free their physiological calprotectin.

The buffer used in step b) may comprise at least one salt of citrate, acetate or maleate, protease-treated serum albumin, and 0.01 to 0.1 percent by weight of one or more anionic surfactants. For improved and accelerated agglutination, one or more of the reaction-components may further comprise an agent facilitating agglutination, e.g. unspecific IgM, rheumatoid factor (RF). Although RF can exist as IgG, IgM, IgA and IgE isotypes, the IgM-class RF is preferred for clinical measurement of calprotectin.

The second reagent component may comprises one or more monoclonal anti-calprotectin antibodies immobilized on nanoparticles. At least two different monoclonal antibodies are preferred for overall safety reasons. If one specific monoclonal antibody only is used, there is always the risk of an untypical immune reaction and a false diagnostic result which risk can be ameliorated by the use of a second specific monoclonal against calprotectin. Moreover, the agglutination reaction is more secure with two specific antibodies as those have different epitopes and binding determinants.

The nanoparticles may have diameters from 150 to 350 nm for increased sensitivity. Nanoparticles with homogenous diameter are preferred. For an increased measurement range, it may be preferable employing monoclonal anti-calprotectin antibodies immobilized on two types of particles having diameters in the ranges from i) 150 to 200 nm and ii) from 250 to 350 nm. Said mono- or multiple sized particles may be carboxylated polystyrene or chloromethyl-activated polystyrene particles.

Another aspect pertains to kit of two reagent-components for measuring calprotectin in a body fluid or sample by a particle-enhanced turbidimetric immunoassay. The first reagent-component may be an extraction buffer as described above and/or comprising 20 to 1000 mmol/L salt of a buffer reagent as described with a pH in the range from 5.0 to 6.0; 50 to 300 mmol/L sodium, potassium or lithium ions; 0.1 to 1.5% protease-treated serum albumin; 0.01 to 0.1% (w/v) anionic detergent, preferably sodium dodecyl sulfate, and optionally beta-aldoses, triose, tetroses, pentoses, hexoses, glucan, dextran and/or sugar to achieve an osmolality of at least 200 mosmos/L. The second reagent component may comprise 0.01 to 0.5% (w/v) latex particles of 150 to 350 nm diameter carrying immobilized monoclonal antibodies against human calprotectin which bind either one of S100A8 and S100A9 or calprotectin (S100A8/A9) at a pH between 5.0 and 6.0.

The method of measuring the presence of calprotectin in a biological sample of a patient, comprises the steps of: (a) collecting a predetermined amount of said biological sample, which may faeces, serum or synovial fluid; b) solubilizing and extracting said biological sample in a pre-determined amount of organic buffer having i) a pH between 5.0 and 6.0, ii) an osmolality of at least 150 mmosM/kg of $H_2O$, iii) which organic acid can coordinate or sequester zinc and calcium ions, and iv) 0.01 to 0.1% percent by weight of an anionic surfactant and, optionally, homogenizing and extracting the matrix of said biological sample followed by a removal of any particulate material to obtain a sample solution containing calprotectin (S100A8/A9); c) mixing a defined amount of said sample solution of step (b) with an amount of particle-containing reagent to form a mixture having i) a pH between 5.0 and 6.0, ii) an osmolality of at least 150 mmosM/kg of $H_2O$, iii) organic salts and acids which sequester calcium and zinc ions, and iv) comprising nanoparticles having diameters of at least 150 to 350 nm and immobilized thereon monoclonal antibodies or fragments thereof which specifically bind either one of the S100A8 and S100A9 proteins or calprotectin (S100A8/A9); d) incubating the mixture of step c) for a first interval of time; and e) acquiring an optical property of said mixture and determining a signal indicative of the content of calprotectin (S100As/A9) based on the optical property of said mixture; f) relating said content to a calibrated control of calprotectin in the same buffer solution and assessing the clinical condition of said patient based on the measured presence of calprotectin (S100A8/A9) in said biological sample.

Another aspect relates to a set of immunological latex turbidimetry reagents for an automated analysis as well as the use of those reagents. The said embodiment may be a two reagent system composed of a first reagent-component containing a buffer for stabilizing the dimer form of calprotectin in said sample solution of step b) and a second reagent-component containing particles carrying immobilized one or more monoclonal antibodies against S100A8 and S100A9 or calprotectin (S100A8/A9). The described method may encompass a transfer or dilution of an extract of the biological sample in the first reagent-component, optionally, after removal of any solid material present. The first reagent-component may comprise protease-treated bovine or human serum albumin, preferably in an amount of 0.1 to 1.5%, in an organic buffer system having a pH in the range from 5.0 to 6.0 and comprising an organic buffer reagents sequestering calcium and zinc ions.

As mentioned, the nanoparticles used may be carboxylated polystyrene particles with diameters ranging from 150 to 350 nm, preferably from 150 to 200 nm. In a most preferred embodiment, said carboxylated polystyrene nanoparticles have diameters ranging from 160 to 180 nm. In a most preferred embodiment, the nanoparticles are substantially of same size, preferably with diameters ranging from 160 to 180 nm. This particle size allows for enhanced presentation of antibody molecules and minimizes the pitfalls of determination in antigen excess conditions. Since such nanoparticles have a large antigen-interaction surface, less antibody-coated particles are required and the antibody-antigen reaction becomes comparable with a surface-mediated immune reaction which is typically faster. Such large particles are also preferred for better metrological traceability of measured values to previous calprotectin measurements using an immunosorbent assay (e.g. ELISA) and for commutability. Traceability, certainty and commutability cannot be achieved when the antibody-antigen reaction is in 3D in liquid and not surface-dependent. Consequently, the authors believe that the use of larger particles than usual improves metrological traceability of results. Result comparability must be realized and represents the core activity of clinical laboratories.

Nanoparticles of sizes are preferred which are suitable for a specific two-dimensional reaction between said monoclonal antibodies and essentially heterodimeric calprotectin and optimized in that less antibodies are needed. The particle-enhanced immune reaction is promoted while steric effects seem to reduce the impact of the calprotectin structure. The increase in size of the particles is not associated with a higher degree of spontaneous turbidity if within the given range of particle sizes.

In a preferred embodiment, said nanoparticles may be of two different sizes having diameters from i) 250 to 350 nm and ii) from 160 to 250 nm. The combination of immunosensitized particles of different sizes should further enhance accuracy as well as measurement range.

Calprotectin is expressed by granulocytes, a subgroup of white blood cells, and prior its release or secretion stored within cytoplasmic granules, likely some sort of compartments of the endoplasmic reticulum and trans Golgi network but this is still under investigation. Granulocytes however have obtained their name by the presence of granules in their cytoplasm. Granulocytes are also called polymorphonuclear leukocytes in line with their varying shapes of the nucleus. The term polymorphonuclear leukocyte usually refers to "neutrophil granulocytes", which account for about 95% of the granulocytes. The other granulocytes subdivided into eosinophilic and basophilic granulocytes and mast cells, which have lower numbers. Granulocytes are produced via granulopoiesis in the bone marrow and stay in circulation for about 6 hours where they perform their biological functions. Calcium ion levels in the cytosol of cells are kept relatively constant, within a cell being 100,000 times lower than outside the cell. It is well-known that increases in calcium ions within the cell can bring about important cellular changes so that calcium ions and intracellular calcium levels are said to be a second messenger. It is vital for the functions of the granulocytes and its calcium-binding proteins such as calprotection that intracellular calcium ion levels are controlled tightly. A strict control of the calcium environment available for binding by calprotectin seems therefore crucial for its functions and structure and for reproducible determination of the biologically effective calprotectin in bodily fluids (serum, synovial fluid, etc.) as well as in biological matrices such as tissue and faeces.

On the other hand, the use of phosphates, e.g. sodium tripolyphosphate (STP) in detergent formulations may lead to precipitates if calcium is present. At low pH. S100A8 and S100A9 are strong calcium-binders and have isoelectric points at pH 6.3 and pH 6.5. Consequently, these proteins have already bound the calcium ion and any addition calcium present in the biological samples (serum, feces, synovial fluids, etc.) may interfere with its quantitative determination. While not wishing to be bound by theory it seems beneficial to inhibit additional calcium binding and oligomerization by a change of the pH below isoelectric points, more precisely, below a pH of 6.0, and that mild sequestration agent is need to avoid precipitates of calcium. This can be achieved by using citrate, maleate or malic buffers. Alternatively, polymers and copolymers of acrylate and maleate may be added to inhibit precipitates and calcium ions-induced agglutination, Calcium complexation depends on the pH of the solution. In the case of citric acid, the concentration of uncomplexed calcium remains weak and constant at pH higher than 6.5, when the total deprotonation of the three carboxylic groups is effective. In the case of malic and lactic acids and at pH higher than the latter deprotonation constant, the free calcium concentration is more important and fluctuating. A number of polycarboxylic acids containing acetal functions have been studied and their calcium sequestering behavior compared. The calcium sequestration by oxidized carbohydrates is generally less than that by corresponding ether polycarboxylates.

When calprotectin is determined in stool, the amount of calcium for binding by calprotectin is dependent on the calcium levels in the gastrointestinal (GI) tract and greatly varies between specimens. Most calcium salts, say the natural calcium sources in supplements and food, have pH-dependent solubility. The solubility of the four major calcium salts (calcium oxalate hydrate, calcium citrate tetrahydrate, calcium phosphate, calcium glycerophosphate) increases in each case with pH. Consequently, a low pH is preferred for extraction and measurement since any free calcium may lead to the formation of untypical tetramers or oligomers of the low-molecular weight S100A8 and S100A9 calcium-binding proteins.

The second reagent-component may be a suspension of latex-particles carrying immobilized antibody. An embodiment of the immunological latex turbidimetry reagent may be first reagent-component containing from 0.1 to 1.5% protease-treated human serum albumin, 20 to 1000 mmol/L citrate buffer, pH 5.0, 50 to 300 mmol/L sodium chloride and 0.1% (w/v) sodium dodecyl sulfate. The second reagent-component may comprise 20 to 1000 mmol/L citrate buffer, pH 5.0; 50 to 300 mmol/L sodium chloride, and 0.01 to 0.5% (w/v) latex particles of 150 to 350 nm diameter carrying immobilized monoclonal antibodies which bind either one of S100A8 and S100A9 or calprotectin (S100A8/A9) heterodimer.

Such reagent-components provide high sensitivity and specificity for calprotectin (S100A8/A9) and improved diagnostic reliability in a particle-enhanced turbidimetric immunoassay which makes use of monoclonal anti-antibodies against calprotectin (MRP 8/14, S100A8/A9) as e.g. commercially available from Immundiagnostik AG, Bensheim, DE (Art. K6927, K6936). More precisely, the diagnostic results with such a homogenous immunoassay are comparable, even more precise, with established ELISA methods and point-of care immunochromatographic tests. A diagnostic cut-off value of 50 micrograms/g stool can be set for the presence of an inflammation. The particle-enhanced turbidimetric immunoassay employs compared with the prior art standardized monoclonals against calprotectin heterodimer (S100A8/A9) immobilized on large nanoparticles having diameters in the range of 150 to 350 nm.

As calprotectin occurs preferably in bodily fluids and faeces as heterodimer the agglutination must not break-up the complexes. It seems that large nanoparticles in the range from 150 to 350 nm make the agglutination kinetically surface-dependent ("two-dimensional") so that the turbidity becomes homogenous and metrological traceable to the calprotectin (S100A8/A9) concentration as determined by an standard ELISA. Thus, diagnostic results and assessments are commutable which is essential for the clinical laboratory work. Consequently, established diagnostic cut-off values can therefore be used.

In summary, the diagnostic results are comparable and commutable to those of established ELISAs using monoclonals while the turbidimetric immunoassay is not only a homogenous assay. The amount of calprotectin (S100A8/A9) present in the sample can be determined by determining the agglutination or opacity/turbidity of the sample with reference to a standard. The analysis can therefore be performed in any commercial automated analyzer such as Hitachi or Cobas®. The use of recombinant antibodies and fragments is preferred in view of the amounts of antibodies required.

A stabilized calprotectin during extraction from faeces and thereafter may be achieved by $Ca^{2+}$ in the extraction and reaction buffers. Biological samples (serum, blood, synovial liquid, or stool) however comprise endogenous calcium. The use of a buffer mildly chelating calcium ions is preferred. Faecal calprotectin (S100A8/A9) is only protected against proteases when having bound calcium ions whereas excess of calcium ions leads to the formation tetramers and oligomers. It seems that an acidic buffer sequestering calcium can stabilize and support the calprotectin (S100A/A9) heterodimer. The stabilizing acid buffer may have a pH between 5.0 and 6.0 and up to 0.5%, preferably 0.1% of an ionic and anionic surfactant. The ionic surfactant may be SDS and the non-ionic surfactant Tween®20. A pH between 5.0 and 6.0 and an ionic strength above 150 mosm/L are also observed in the granules of granulocytes so that the conditions for solubilization and measurement are similar the milieu in the secretory granules.

In the following; some terms as used in the description are further explained and defined:

The term body sample or body fluid" describe human or animal material including blood, serum, plasma, faeces, urine, saliva, excreta, body and tissue fluids. Body samples are also extracts of material and specimen for diagnostic examination or evaluation and identification of a medical condition. The sample may be liquid or solid. In case of a solid or semi-solid matrix (faecal sample), the sample must be extracted. Any commercially stool sample extraction kit may be used, e.g. stool sample prepration system (SSPS) pre-filled with IDK Extract® (Immundiagnostik AG, Bensheim, DE) or manually with a first reaction-component as described in herein. The amount necessary for performing a turbidimetric test ranges from 5-20 mg extracted stool. The sample may be urine for studying diseases of the intestinal tract, liver, gall, pancreas or kidney. The sample may be blood, plasma or serum for studying cardiovascular diseases.

Calibrators are (serial) solutions with known concentrations of the analyte (calprotectin) and equally required for accurate performance in the laboratory work. In order to interpret the signal strength and, thereby, to determine the presence or concentration of analyte (calprotectin) in the sample, the result with a specimen of a body sample is compared to those obtained with a serial dilution of the calibrator.

Detection limit is defined as the lowest amount of analyte that can be reliably detected in the assay at which total the error is in agreement with the accuracy requirements. A detection limit of ≤10 micrograms calprotectin/gram stool can be obtained according to the described method which reasonable below the cut-off (50 micrograms calprotectin/gram stool) for diagnosis of an inflammation in stool.

Turbidimetry is the measuring of the loss of intensity of transmitted light due to the scattering effect of particles suspended in a solution. Light of known wavelength (nm) is passed through a cuvette containing the solution with particles and collected by a photoelectric cell. A measurement value (mE) is given for the amount of absorbed light. Two types of turbidimetric assays are currently used, direct and particle-enhanced immunoturbidimetry (PETIA). In direct immunoturbidimetry, antibodies form an immune complex by direct interaction with their corresponding antigens. The particle-enhanced immunoturbidimetric method is based on the coating of nanoparticles with antibodies, in the present application with two mouse monoclonal antibodies against calprotectin. Particle-enhanced immunoturbidimetric assays come into place when the analyte is present in low concentration as the particles amplify the signal and produce an increased sensitivity.

Nanoparticles are generally used whose mean diameter is typically measured in nanometers (nm). The size (diameters) of nanoparticles can reliably by dynamic light scattering (DLS), photon correlation spectroscopy (PCS) or quasi-elastic light scattering (QELS). Diameters as described herein have been measured employing a Malvern Zetasizer Nano (Malvern Panalaytical Ltd., Malvern, GB) or Horiba SZ-100, the Gaussian deviation from the given mean being less 10 nm. As the surface of the nanoparticle are conjugated with biomolecules (HAS) and, of course, immunoglobulins (Ig) and monoclonals, the diameters must be strictly determined and controlled. A large surface area-to-volume ratio of a nanoparticle-Ig-bioconjugate is advantageous for interaction with the immunoglobulins with target biomolecules. The preparation of antibody-carrying nanoparticles is well known in the art. The antibodies can be absorbed by a suitable coating on the particles, or it may be chemically coupled thereto through a bridging agent. The antibodies may also be coupled directly to the polymer of the latex particle itself. Said nanoparticles may be stored prior use in a buffer comprising sodium citrate tribasic dehydrate, bovine serum albumin, Tween 20, sucrose, sodium azide (Storage buffer). By use of the inventive storage buffer, latex immunoparticles with monoclonal antibodies against calprotectin are highly stable in suspension, i.e. no spontaneous aggregation, for periods up to 12 months at 2-8° C. prior immunoassay, while preserving antibody stability.

Calprotectin is released by granulocytes and prior release stored within cell granules, more precisely likely compartments of the trans Golgi which are not lysosomes. Calcium ion levels in the cytosol and within those acidic compartments (pH 5.0 to 6.0) are kept relatively constant, with the concentration of calcium ions being 100,000 times smaller than outside the cell. It is vital for the functions of the granulocytes, as well as for other cells, that intracellular calcium ion levels are controlled tightly. A tight control of the calcium ions available to binding by calprotectin and of the pH is likewise crucial, not just for its functions, but also for a metrologically traceable determination of calprotectin in body samples. Consequently, monoclonal antibodies against calprotectin must be used which bind at low pH. Thus, there is a need to stabilize the soluble form of calprotectin during extraction from the sample matrix and in the assay solution where immunoreaction and subsequent agglutination takes place. This may be achieved by adding up 0.5%, preferably 0.1% of ionic and non-ionic surfactant. A preferred anionic surfactant is SDS, while the prior art seems to work primarily with non-ionic surfactants such as Tween®20. A pH between 5.0 and 6.0 is used for extraction and such a pH is also observed in the acidic compartments and granules of granulocytes.

For a reduction of unspecific immunoreactions, the sample may be dissolved in a buffer solution comprising anti-IgM-antiserum. The presence of anti-IgM-antiserum may contribute to correct the effect of IgM-interferences in the immunoassay so that consistent results can be obtained regardless of sample origin. Anti-IgM-antiserum may contain endogenous calprotectin so that each batch of anti-IgM antiserum requires eventual correction for IgM-serum related calprotectin content.

The instant disclosure contemplates further a test kit for quantitative determination of calprotectin. The kit may comprise homogenous nanoparticles coated with at least one anti-calprotectin monoclonal antibody, or antibody fragments thereof, binding at pH between 5.0 and 6.0, wherein said nanoparticles have diameters ranging from 160 to 180 nm. For increased sensitivity and measurement range the kit may comprise a second type of homogenous nanoparticles having another homogenous diameters. The disclosure also pertains to an method for quantitative detection of calprotectin in stool comprising the steps of a) extracting a defined amount of stool with a first reaction-component to solubilize calprotectin and provide a liquid sample, the first reaction-component having a pH of 5.0 to 6.0 and an osmolality of at least 150 mosm/L; b) contacting said liquid sample with nanoparticles having immobilized at least one monoclonal antibody against calprotectin (S100A8/A9) which binds at pH 5.0 to 6.0; and c) assessing the amount of calprotectin in the sample by turbidimetry, wherein the diameters of said nanoparticles are in the range from 160 to 350 nm. In a preferred embodiment said nanoparticles may be carboxylated polystyrene particles and for the sake of sensitivity and detection rage, there may be two types of homogenously sized nanoparticles, their homogenous diameters being in the range from i) 150 to 250 nm and ii) from 250 to 350 nm. The latex particles may be particles of organic high-molecular weight materials, such as latex particles of polystyrene, styrenemethacrylic acid copolymer, styrene-glycidyl (meth) acrylate copolymer, or styrene-styrene sulfate copolymer.

Such a test and method can be adapted to automated analyzers in clinical laboratories. The method is characterized by reduced unspecific agglutionation due to the use of monoclonals which are not lot-specific and bind to one single epitope only. Conventional turbidimetric tests employ avian polyclonal antibodies (chicken IgY against the hetero dimer of MRP8/MRP14) which suffer from spontaneous aggregation in the turbidimetric assay. Moreover, a reaction buffer at physiological pH (3-(N-morpholino)propane sulfonic (MOPS) buffer with pH 7.2) is used in the prior art, which does not interfere with an aggregation of the S100A9 and S100A9 proteins to multi-homo and -heteromers (Nilsen T et al, *A new turbidimetric immunoassay for serum calprotectin for fully automized clinical analysers*, J. Inflammation, 2015, 12: 45). The same can be observed when calprotectin is diluted in a buffer at physiological pH 8R1: pH 7.2; R2, pH 8.1) as used by the Bühlmann fCal® turbo, which employs the same avian polyclonal antibodies. The turbidimetric method and reaction, however, determines the number of target molecules (complex) in solution and not the amount of protein (amino acids) as is determined for calibration by the Biuret method. Consequently, conventional turbidimetric methods for determination of calprotectin using a high pH and polyclonal antibodies can give no metrologically traceable results. Commutability of results between conventional methods can only be achieved by correction factors (ex post facto) which are not available in the clinical laboratory routine. Moreover, lot variation between different batches of antibodies raised and purified with different lots of calprotectin antigen in different batches is critical.

In one embodiment of the invention, the nanoparticles may be latex particles. In a preferred embodiment, the latex nanoparticles are carboxylated polystyrene particles with a particle size from 150 to 250 nm (250 to 350 nm), surface charge density from 40 to 60 µC/cm$^2$; surface charge density: 150-250 µEq/g, solids content 10.0(%); stabilized with 0.05% of sodium azide.

The inventive turbidimetric method requires no dedicated analyzer, since it is flexibly applicable to common photometric analyzers. According to the present invention, additional costs for purchasing a dedicated instrument or consumables are no longer necessary. The present method facilitates fully automated processing, without time-consuming sample splitting, thereby allowing higher sample throughput and increasing clinical laboratory efficiency. On basis of the present disclosure, exact quantification, metrological traceability, commutability of results and diagnostic differentiation on the basis of a cut-off value (e.g. 50 micrograms calprotectin/gram stool) is feasible. Such is need for therapeutic monitoring of patients. Automation and standardization are applicable and preferred embodiments since manual testing involves high contamination risk for the user and the analyzed sample.

One object of the present application is the provision of a particle enhanced turbidimetric immunoassay which is based on mammalian monoclonal antibodies against human calprotectin which avoids the disadvantage of reduced assay sensitivity as is typically incurred with avian antibodies. Another object provided is an assay for determination of calprotectin which can be applied on any standard chemistry analyser in a manufacturer-independent manner. Another aspect is a storage buffer for latex particles with immobilized antibodies, eliminating the natural tendency of latex particles to aggregate and precipitate spontaneously upon storage. The described reaction buffer can also be used as storage buffer.

The counting of leukocytes and/or measurement of C-reactive protein (CRP) measurement are currently used for diagnosis of a bacterial infection requiring antibiotic treatment. It has been estimated that about 40% of such cases are misclassified as bacterial infections and other causes (XuS et al, *Lipocalins as biochemical markers of disease*, Biochim Biophys Acto 2000, 1482:298-307). The neutrophil activation marker HNL/NGAL would allow distinction between acute bacterial and viral infections but is no viable marker due to its very low concentration in body samples. The present assay for calprotectin reflects granulocyte activation and has been shown to be elevated in inflammatory conditions. The human calprotectin molecule, however, has been described as a 24 kDa hetero dimer comprising subunits S100A8 (MRP8) and S100A9 (MRP14) but there is no consensus on the actual structure of calprotectin in vivo as the measurement by turbidimetry requires a defined standard and molecules. Calprotectin can, according to the authors, be found as a heterodimer, a heterotrimer or even a heterotetramer when calcium is present. Calprotectin is a calcium-binding protein found in neutrophilic granulocytes that becomes available in the intestinal lumen via leukocyte shedding, active secretion, cell disturbance, and cell death. During intestinal inflammation, neutrophilic granulocytes migrate into the intestinal mucosa and elevate the faecal calprotectin levels.

Faecal calprotectin levels correlate with histologic and endoscopic assessment of disease activity in Morbus Crohn's disease and ulcerative colitis. Faecal excretion of indium-111-labelled neutrophilic granulocytes has been suggested as the "gold standard" of disease activity in inflammatory bowel disease (IBD). As patients with active inflammatory bowel diseases (IBD) may have up to 10-fold increase in faecal calprotectin levels, a commutable determination of elevated calprotectin concentrations in faeces is need. Faecal calprotectin is also used to discriminate between IBD and irritable bowel syndrome. Due to its resistance to enzymatic degradation but only if calcium has been bound, calprotectin can be extracted and measured in faeces. Calprotectin can also indicate other inflammatory gastrointestinal conditions such as colorectal cancer, gastroenteritis, and food intolerance, but its levels vary depending on age and day-to-day within individuals. Serum calprotectin is a valuable inflammatory marker for the diagnosis of sepsis and acute appendicitis. There is however no international calprotectin standard. Therefore, internally established standards for calibration are being used to avoid inaccurate determinations due to batch variations. This also leads to different levels of standards among manufacturers depending on which method is chosen.

The determination of calprotectin as disclosed, however, provides metrologically traceable results. One side aspect is therefore a validation of the turbidimetric assay performance by calprotectin calibrators from 0 to 2000 µg/ml sample, which is necessary to overcome the high variability of the calprotectin content among different biological samples. The large range avoid excessive runs or antigen excess problems and may be achieved with the described method.

Figure 2:
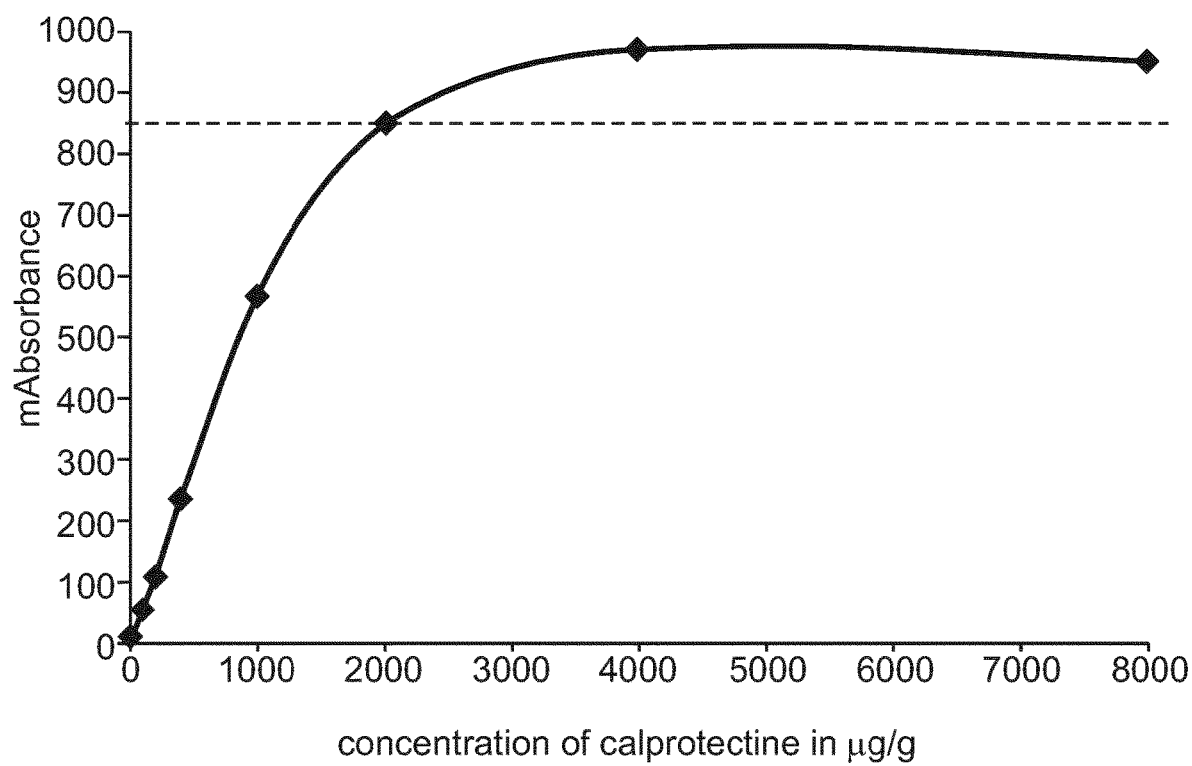
FIG. 2 shows a calibration curve for a turbidimetric assay with a mouse monoclonal antibody against calprotectin and the prozone limit of the immunoassay.

FIG. 1 shows a calibration curve with mouse monoclonal antibody-coated latex particles. The absorbance values (Y axis) correspond to calprotectin values in micrograms calprotectin/g stool (X axis). The results support a continuous behaviour in the range from 0 to 2000 µg/g The performance of the immunoassay loses linearity when calprotectin concentrations in the sample are above 2000 µg/g stool as shown in FIG. 2.

The immunoparticles of the invention are coated with mouse monoclonal antibodies raised against MRP8/MRP14 calprotectin. While avian antibodies are less reactive with rheumatoid factor or human anti-mouse IgG antibodies or the human complement system (see EP 1 573 335 B1)—well-known causes of erroneous measurement—polyclonal avian antibodies are less specific than mammalian monoclonal antibodies. Another object by the present disclosure is therefore the provision of a turbidimetric calprotectin assay which is based on highly specific antibodies without the disadvantage of unspecific reactivity. This is achieved by the present assay system.

Figure 3:
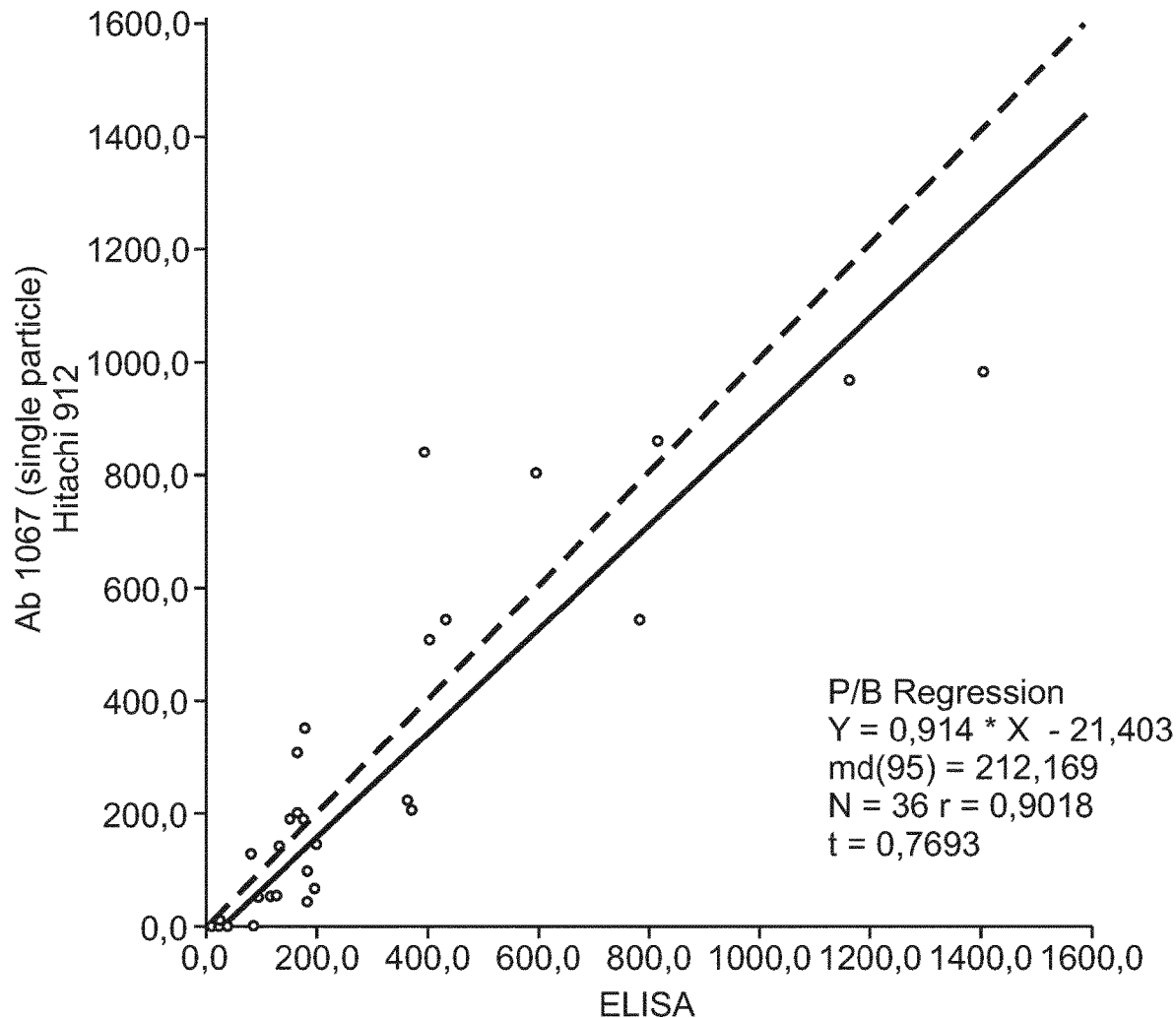
FIG. 3 is a plot showing the correlation of the turbidimetric immunoassay employing one monoclonal antibody and a conventional ELISA using two monoclonals as capture and detection antibodies for determination of standard calprotectin from granulocytes with intact acidic compartments.

Sensitive methods for measuring calprotectin are available. The available ELISA assays are however associated with long test turn-around times and more laborious than turbidimetric assays. The present disclosure provides an assay system wherein samples can be processed upon their arrival to the laboratory so that any medical condition associated with elevated calprotectin levels can be timely diagnosed. The suitability of the turbidimetric method was tested in 36 stool samples and correlated with a standard ELISA assay as reference. FIG. 3 shows the correlation between the turbidimetric assay with one monoclonal antibody-coated particle size and an ELISA assay for determination of calprotectin. For the turbidimetric assay an Application Hitachi 912 was used according to the manufacturer. Statistical analysis revealed commutable results, thus, confirming the suitability of the disclosed method for determination of calprotectin in stool (P/B regression Y=0.914*X−21,403; md(95)=212,169; n=36; r=0.9018, t=0.7693). Of note, the correlation coefficient r ranges from −1 (0) to 1. A value of 1 indicates that the relationship between X and Y is perfectly described by a linear equation. A value of 0 refers to non linear correlation between the variables.

Figure 4:
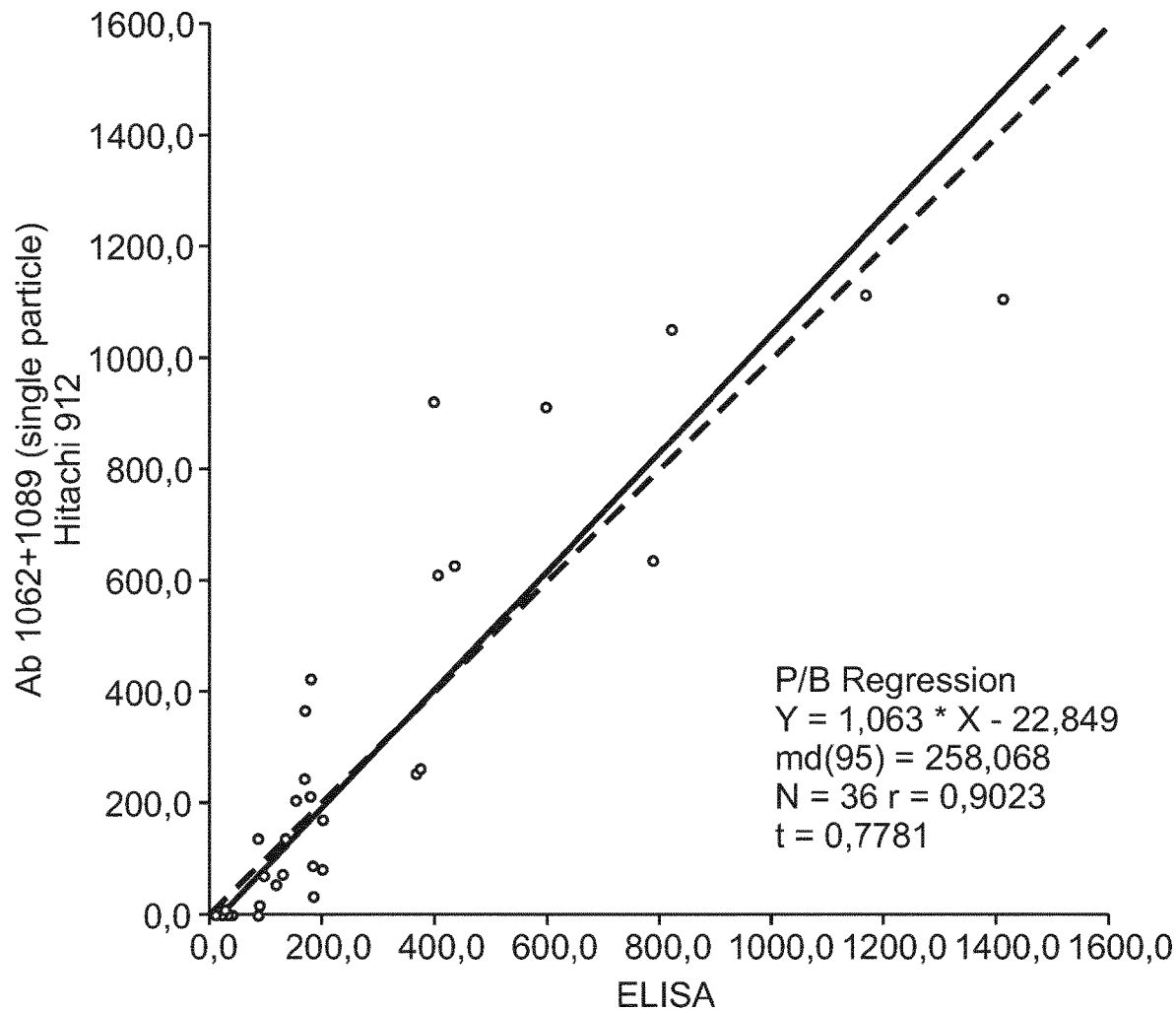
FIG. 4 is a plot showing the correlation of the turbidimetric assay with two monoclonal antibodies and a conventional ELISA assay for determination of standard calprotectin isolated from granulocytes with intact lysosomal membranes.

In a further experiment, in which latex-particles of a single size were coated with two different monoclonal antibodies against calprotectin, the turbidimetric method was tested with 36 stool samples and determined results correlated with a standard ELISA assay as reference. FIG. 4 shows the correlation of the turbidimetric assay measurements with one and two monoclonal antibodies and a corresponding ELISA for calprotectin. Statistical analysis of the assays revealed no significant difference between the use of one (FIG. 3) or two antibodies (FIG. 4). The slight increase in assay sensitivity with two antibodies is likely for a higher signal intensity due to increased antibody charge (P/B regression Y=1,063*X−22,849; md(95)=258,068; n=36; r=0.9023, t=0.7781).

Figure 5:
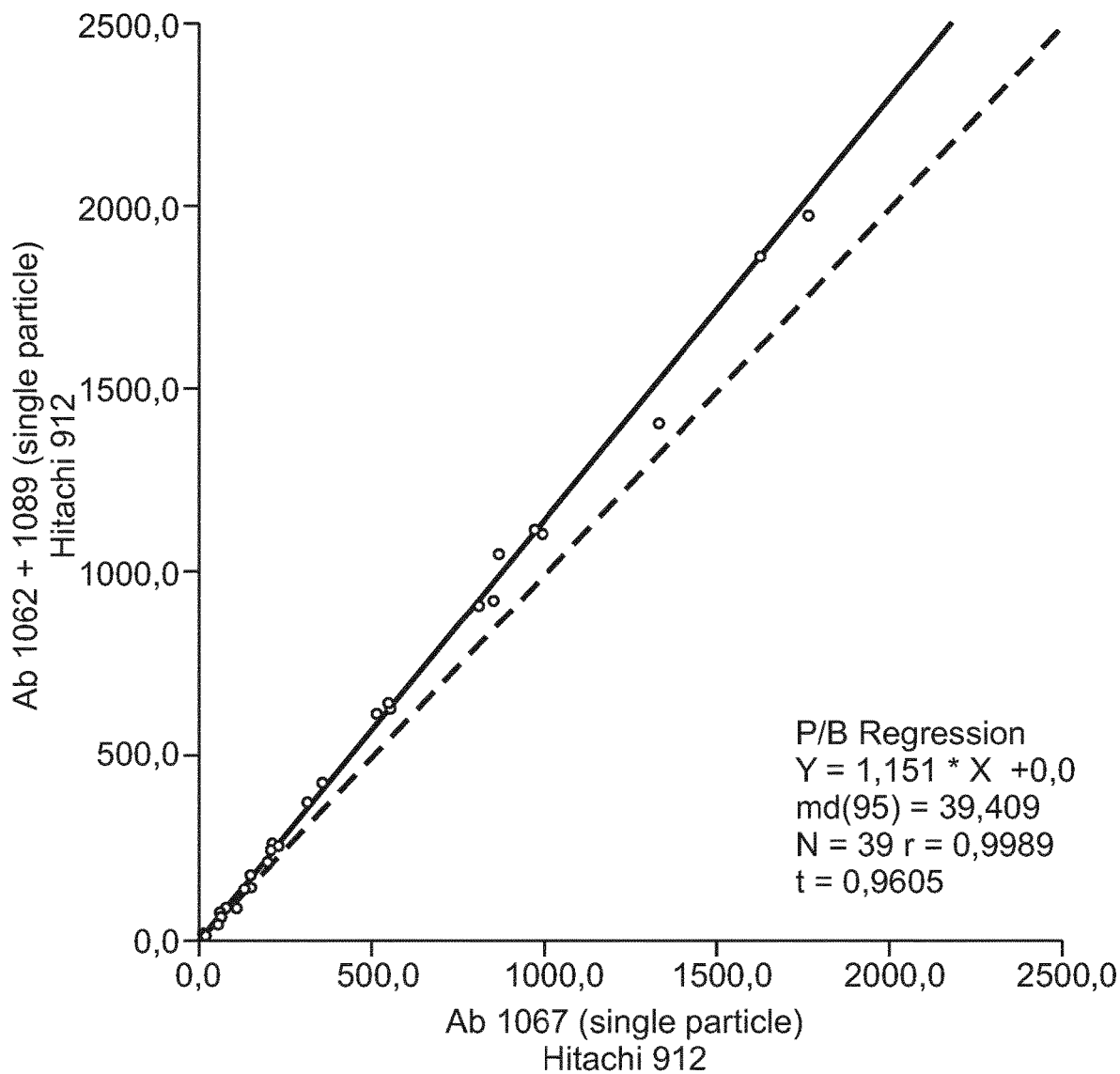
FIG. 5 is a plot showing the measurement correlation of the turbidimetric assay for determination of calprotectin according to the invention with two monoclonal antibodies and one monoclonal antibody.

Further, latex particles of single size were coated with a) two monoclonal antibodies and b) one single monoclonal antibody (mAB Nos. 1062, 1067, 1068, 1089 of Immundiagnostik AG, Bensheim, DE). 39 stool samples were extracted and incubated with latex particles of either condition. The turbidimetry assay according to the invention was performed, in both conditions, using Application Hitachi 912. FIG. 5 shows the correlation analysis of the turbidimetric assay (P/B regression Y=1,151*X+0.0; md(95)=39,409; n=39; r=0.9989; t=0.9605). Additional experiments resulted in similar statistical values as shown in Table 1.

TABLE 1

| Monoclonal antibody Nr. | Y | X | md(95) | n | r | t |
|---|---|---|---|---|---|---|
| 1067 Vs 1062 + 1089 | 1.151 | 0.0 | 39.409 | 39 | 0.9989 | 0.9605 |
| 1067 Vs 1067 + 1068 | 1.014 | 0.0 | 14.472 | 61 | 0.9997 | 0.9748 |
| 1068 Vs 1067 + 1068 | 1.008 | +9.051 | 22.799 | 61 | 0.9994 | 0.9617 |

Figure 6:
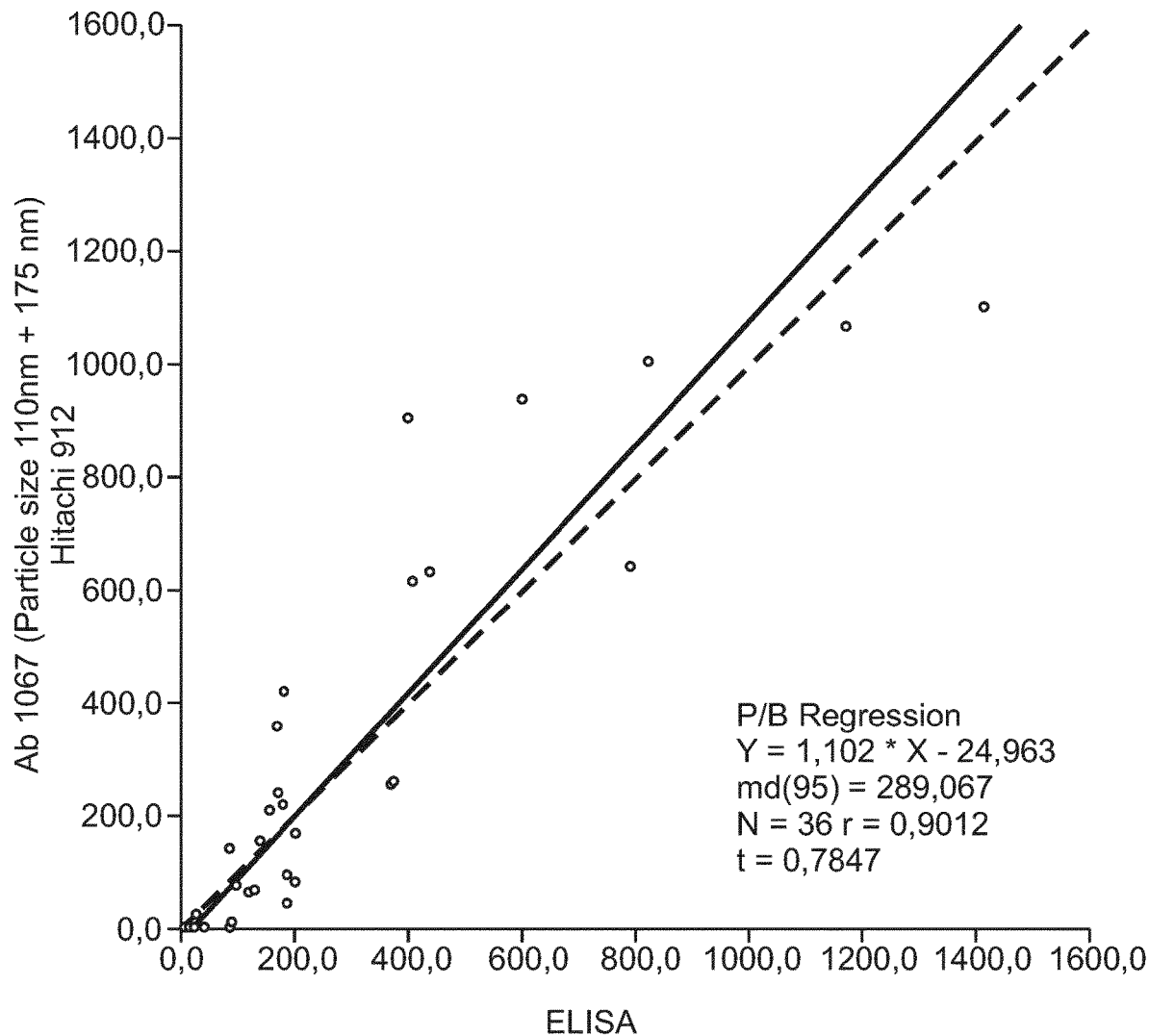
FIG. 6 is a plot showing the measurement correlation of the described, employing two types of particle of different sizes and a conventional ELISA assay for determination of calprotectin.

The performance of the turbidimetry assay with immunoparticles of two different sizes (heterogeneous) coated with a single monoclonal antibody was tested in 36 stool samples and correlated with a standard ELISA assay as reference. For the turbidimetric assay, Application Hitachi 912 was used according to the manufacturer. FIG. 6 shows the correlation analysis of the turbidimetric assay. Statistical analysis of the test revealed commutable results, thus, confirming the method for accurate determination of calprotectin in stool (P/B regression Y=1,102*X−24,963; md(95) =289,067, n=36; r=0.9012; t=0.7847).

The turbidimetric method was further tested and calprotectin measurements performed with latex-particles of two different sizes (heterogeneous) and compared to one employing a single particle size (homogeneous). Latex-particles of 250 nm and 175 nm were coated with a single monoclonal antibody against calprotectin. Samples with calprotectin concentrations ranging from 0 to 2000 µg/g were used as calibrators for the turbidimetric assay using Application Hitachi 912 according to the manufacturer's instructions. As shown in Table 2 (mE (mA): mAbsorbance), assay performance with latex-particles of two different sizes results in increased determination sensitivity as compared to single-size particles. Accordingly, the combination of at least two particles sizes may result in improved detection range of calprotectin compared to the use of single size particles.

Latex nanoparticles have a tendency to self aggregate. The disclosed storage buffer may comprise sodium citrate tribasic dehydrate, at pH 5.0, bovine serum albumin, 1% SDS, sucrose, sodium azide. The storage buffer of the disclosure contributes to increase the storage stability of the latex immunoparticles for long periods of time. Immunoparticle stability disclosure means that spontaneous latex-particle aggregation (turbidity) is reduced so that the second reaction-component may be stored up to 12 months at 2-8° C. prior use. The storage buffer is particle stable at 37° C. for several days. Not only aggregation is reduced but antibody stability can be extended resulting in measurement values pretty independently from storage conditions.

TABLE 2

| Calprotectin (µg/g) | 110 nm + 175 nm (mE) | 175 nm (mE) |
|---|---|---|
| 0 | 11.3 | 9.2 |
| 100 | 52.1 | 47.5 |
| 200 | 111.4 | 103.9 |
| 400 | 218.1 | 212.6 |
| 1000 | 456.1 | 443.7 |
| 2000 | 681.9 | 672.2 |
| 4000 | 768.7 | 757.9 |
| 8000 | 748.2 | 724.3 |

TABLE 2-continued

| Calprotectin (µg/g) | 110 nm + 175 nm (mE) | 175 nm (mE) |
|---|---|---|
| 12000 | 715.3 | 695.1 |
| 16000 | 629.7 | 689.8 |

Table 3 shows absorbance values (mE) measured at storage day 1 and 30 at 2-8° C. using immunoparticles coated with two monoclonal antibodies in a turbidimetry assay according to the invention. Immunoparticles were preserved i) at 2-8° C. for 30 days and ii) kept at 37° C. for 3 days and further 30 days at 2-8° C. Taking in consideration that monoclonal antibodies are temperature sensitive, this suggests that the storage buffer of the disclosure contributes to an accurate determination of calprotectin at different levels, namely immunoparticle aggregation and particle-bound antibody stability.

TABLE 3

| Calprotectin | Storage buffer 2-8° C. | | Storage buffer 37° C. | |
|---|---|---|---|---|
| (µg/g) | Day 1 | Day 30 | Day 1 | Day 30 |
| 0 | 3.4 | 2.1 | 3.4 | −1.1 |
| 100 | 58.5 | 53.6 | 58.5 | 59.7 |
| 200 | 108.4 | 114.3 | 108.4 | 119.1 |
| 400 | 220.3 | 229.8 | 220.3 | 240.4 |
| 1000 | 487.7 | 500 | 487.7 | 531.6 |
| 2000 | 707.9 | 698.2 | 707.9 | 732.9 |
| 4000 | 818.4 | 790.1 | 818.4 | 814.7 |

If the analyte exceeds a certain concentration in the sample, antibody saturation occurs, followed by decreased aggregation. A lowered aggregation results in lower intensity signals. This effect is described as "antigen excess" and may lead to misinterpretation of falsely low values and to wrong diagnostic decisions. As disclosed, an excess of target antigen does not necessarily interfere with the turbidimetric determination since the nanoparticles are optimally dispersed and separated from each other, also by their charged surfaces, leaving the whole surface of the particle free for antigen binding. An increase in antibody binding capacity is achieved by the disclosed buffer for particle storage and test reaction.

In a preferred embodiment, the method of the invention is performed with antibody-coated nanoparticles of sizes ranging from 150 to 350 nm. The prior art teaches that nanoparticles for turbidimetric immunoassays may not have more than 140 nm in diameter because an increased particle size would correlate with an unspecific aggregation, in particular, of latex particles. This teaching however must refer to particles carrying less specific or cross-reacting polyclonal antibodies. The instant disclosure however supports nanoparticles having diameters from 150 to 350 nm and that large particles contribute to accurate determination. Also enhanced reaction between the monoclonal antibody and the target antigen (calprotectin) is achieved due to the increased interaction area and because the reaction is partly surface-dependent. Importantly, the size increase is not associated with a higher degree of spontaneous turbidity.

There are, however, no reliable means in the art to enhance the sensitivity of the measurement and to accelerate the dispersion of suspended latex particles without disturbing the immunological reaction. The method of the invention solves this problem by use of a buffer composition (Test buffer or first reaction-component) comprising sodium citrate, pH 5.0 to 6.0, 150 mM NaCl, bovine serum albumin, SDS/Tween®20, sucrose, sodium azide. The present method can be used in combination with a commercially available stool extract buffers (e.g. IDK Extract® Immundiagnostik AG, Bensheim, DE) if mixed with the first reaction-component R1. For comparison, different concentrations of calprotectin calibrators from 0 to 2000 µg/g were separately diluted in Test buffer as disclosed and IDK Extract® buffer. Immunoturbidimetry assays were performed with two different monoclonal antibodies bound to latex particles. As shown in Table 4, a measurable increase in detection sensitivity can be achieved with Test buffer (mA: mAbsorbance values) which points to "more available target molecules" and less multimer formation.

For further comparison, 20 stool samples were separately extracted with the test buffer of the invention and the commercially available Bühlmann extraction buffer (Bühlmann fCal Turbo®) which has a measured physiological pH of 7.2 (Bühlmann Laboratories AG, Basel, Switzerland). The turbidimetric assay was performed as described above using Application Hitachi 912 according to the manufacturer's instructions. The absorbance values in either condition were correlated to each other. Statistical analysis showed correlation between both conditions (P/B Regression Y=1, 004*X−1,552; md(95)=30.37; n=20; r=0.9932; t=0.9524). The Test buffer of the invention, therefore, provides at least as good faecal calprotectin extraction as commercially available buffers but provides the advantage of reduced unspecific immunoparticle aggregation.

TABLE 4

| Calprotectin (µg/g) | Test buffer (mE) | IDK extract (mE) |
|---|---|---|
| 0 | 11.5 | 0.4 |
| 100 | 48.1 | 44.5 |
| 200 | 103.3 | 93.9 |
| 400 | 206.6 | 194.6 |
| 1000 | 456.1 | 435.6 |
| 2000 | 656 | 630.8 |
| 4000 | 759.4 | 730.5 |
| 8000 | 751.8 | 724.8 |
| 12000 | 712.8 | 675.6 |
| 16000 | 673 | 638 |

Faeces contain around 75% water and the remaining solid fraction is 84-93% organic solids. These organic solids consist of: 25-54% bacterial biomass, 2-25% protein or nitrogenous matter, 25% carbohydrate or undigested plant matter and 2-15% lipids. These proportions vary considerably depending on diet and body weight. The remaining solids are composed of calcium and iron phosphates, intestinal secretions, epithelial cells, and mucus. Body sample components, in particular, from stool, may represent a source of interference affecting the sensitivity of immunoassays and PETIA. Such interferences may lead, for example, to negative absorbance values. By the present method, the interference by above described stool sample components is reduced.

Immunoglobulin M (IgM) is a basic antibody produced by B cells. IgM is the largest antibody in the human circulatory system and the first antibody to appear in response to initial exposure to an antigen. The presence of IgM antiserum may contribute to counter sample matrix-related disturbances. However, IgM antiserum may contain endogenous calprotectin. An analysis of every IgM antiserum batch is recommended. Table 5 shows mE absorbance values obtained by turbidimetric measurements of calprotectin calibrators and stool samples diluted in reaction-component, with or without IgM antiserum addition. Negative absorbance values are abolished and a general increase in detection sensitivity and reliability is achieved.

TABLE 5

| Calprotectin (µg/g) | | w/o IgM (mE) | IgM (mE) |
|---|---|---|---|
| Calibrators | 0 | 4.2 | 8.5 |
| | 40 | 31.7 | 27.6 |
| | 100 | 74.2 | 61 |
| | 200 | 160.5 | 134.4 |
| | 400 | 392 | 351.3 |
| | 2000 | 1094.1 | 1082.1 |
| | 4000 | 1211.1 | 1183 |
| | 8000 | 1140.3 | 1128.9 |
| Stool samples | 14 | −10.4 | 2.3 |
| | 22 | −6.5 | 11.7 |
| | 31 | 5.6 | 17.5 |
| | 40 | 82.6 | 67.7 |
| | 57 | 29.5 | 43.3 |

EXAMPLES

Example 1 Production of Immunoparticles Against Calprotectin

Latex particles from well known producers, e.g. MERCK, Bangs Laboratories were used. The latex was carboxylated polystyrene or chloromethyl latex. The latex particles had following parameters: surface charge density 62 µC/cm2; surface charge density 163 µEq/g pol.; solids content 9.0%, stabilized with 0.05% sodium azide. Immunoparticles were prepared by covalently attaching purified monoclonal mouse antibodies (mAB 1062, 1067, 1069, 1089, and binding in first reaction-component) directed against purified human calprotectin from granulocytes with intakt lysosomal membranes The carboxylated polystyrene particles were preferably of uniform size (175 nm). Alternatively, nanoparticles of two different sizes (160 to 175 nm and 250-275 nm) were coated with a single monoclonal antibody (see FIG. 6). Also, latex particles of single size 175 nm were coated with two different monoclonal antibodies.

Particles were kept prior use in Storage buffer comprising sodium citrate, pH 5.0 to 6.0, 50 mM maleate buffer, pH 5.0, 150 mM NaCl, bovine serum albumin, 150 mM sucrose, sodium azide at 2-8° C.

Example 2 Stool Sample Extraction

Stool samples were extracted as follows. 15 mg stool was each diluted 1:100 in 1.5 ml buffer. Empty sample tubes were filled with 1.5 ml of test buffer, 50 mM maleat pH 5.0, 150 mM NaCl, sodium azide, 0.1% sodium dodecyl sulfate, bovine serum albumin, with or without antiserum IgM. For comparison, samples were also extracted using ready-to-use IDK Extract® extraction buffer (Cat. No. K 6967) and Bühlmann fCal Turbo™ extraction buffer at room temperature. Stool samples were collected and stored up to 48 h at 2-8° C. For long term periods (up to 12 months) storage at −20° C. is recommended. Upon start of the turbidimetric assay, frozen samples were slowly thawed, preferably at 2-8° C. In some occasions, heterogeneous samples were homogenized mechanically. For sample collection, IDK® Stool Sample Application System (SAS) (Cat. No. K 6998SAS) was used. The tip of the dipstick of SAS, which has notches that retain a fixed amount of raw material, was inserted into the stool sample. The dipstick was placed back into the tube with extraction buffer. When putting the stick back into the tube, excess material was stripped off. 15 mg stool sample remaining on the dipstick were then diluted in extraction buffer. The tubes were tightly closed and well shaken until no stool sample remained in the notches. 10 minutes were necessary to allow the sediment to settle. Making sure that the sediment was not dispersed again, the extracted sample was diluted 1:25 in test buffer. For example, 40 µl extracted stool sample were added to 960 µl test buffer.

Example 3 Calprotectin Turbidimetric Immunoassay

Samples extracted with either extraction buffer as described above were used for turbidimetric determination using the application Roche Hitachi 912 according to the manufacturer. 10 µL extracted sample were added to 200 µL Test buffer and 50 µL Storage buffer, comprising sodium citrate pH 5.0, bovine serum albumin, Tween 20, sucrose, sodium azide. The automated analyzer mixed immunoparticles gently with the extracted samples while incubating at 37 degrees Celsius for 5 minutes. The second reaction-component with particles carrying immobilized monoclonal antibodies was added, while gently shaking. Time for agglutination was 5 minutes at 37 degrees Celsius during which absorbance was measured. Measurements were performed in duplicates. The absorbance values were obtained reading at 570 nm wavelength.

Commercially available purified calprotectin was diluted in citrate buffer pH=5.4 in a range from 0 to 2000 µg/g. (6 calibration points) for calibration of the turbidimetric assay. A linear range from 30 to 2000 µg/g was obtained.

Stool samples with known amounts of calprotectin were used as control and test samples. Stool samples containing calprotectin were diluted 1:100 in reaction buffer, resulting in measurement ranges from 0.1 to 20 µg calprotectin in 1 g stool. Taking the dilution factor in consideration, the actual measurement range was up to 2000 µg/g.

Reference range 1 g stool is equivalent to 1 ml. The median value in healthy adults is about 25 µg calprotectin/g stool. Samples with a calprotectin concentration below 50 µg/g were regarded as negative. Samples with a calprotectin concentration between 50 µg/g stool and 100 µg/g stool were regarded as borderline positive. Samples with a calprotectin concentration above 100 µg/g stool were regarded as positive.

Example 4 Calprotectin ELISA Assay

ELISA IDK® Calprotectin (MRP8/14) was chosen for comparison with the turbidimetric determination method of the invention. The assay utilizes the two-site sandwich technique with two selected monoclonal antibodies that bind to human calprotectin. Calibrator, controls and diluted patient samples are added to wells of microplate coated with a monoclonal anti-human calprotectin antibody. During the first incubation step, the immobilized antibody molecules bind calprotectin in the samples. Then, a peroxidase labelled conjugate is added to each well and a complex is formed. Tetramethylbenzidine (TMB) is used as a substrate for peroxidase. Finally, an acidic stop solution is added to terminate the reaction. The colour changes from blue to yellow in the presence of calprotectin.

The color intensity was directly proportional to the calprotectin concentration of the sample. Samples were quantified with respect to their optical density. A master calibration curve using a calprotectin calibrator is run with each test. Duplicates were carried out. Absorption was immediately measured with an ELISA reader at 450 nm against 620 nm (or 690 nm) as a reference. Alternative, absorption was measured at 405 nm against 620 nm as a reference when the extinction of the highest standard exceeded the range of the photometer. Of note, the intensity of the color change is temperature sensitive. Protocols according to ELISA IDK® Calprotectin (MRP8/14) Immundiagnostik AG, Bensheim, Germany).

The comparative results were evaluated using Analyse-it for Excel (Analyse-It Software, Ltd, Leeds UK). Passing Bablok regression fit was used for commutability analysis of the tubidimetric assays (and ELISA).

In summary, an immuno turbidimetric assay for calprotectin has been provided, in particular for determination of calprotectin in a faecal matrix or in serum and other body fluids and samples, which is based on mammalian monoclonal antibodies specific for calprotectin as present in the acidic granules of neutrophilic granulocytes. Such monoclonals have been raised against calprotectin subunits at low pH and also bind these subunits at the given pH. Specific calibration of the calprotectin analyte is needed as this analyte can (self)-aggregate and form complex multimers in the presence of calcium which interferes with the turbidimetric measurement. Metrological traceability and commutability of results is required in clinical laboratory work. The authors have found that the described mouse monoclonals bind calprotectin primarily as hetero dimer (S100A8/A9) and that multimer formation can be inhibited by an organic buffer which coordinates calcium ions. The presence of a surfactant is recommended, and most preferred is the addition of an anionic surfactant as the subunits of calprotectin have a pI of 6.1 and 6.3 and the immuno turbidimetric reaction is run at a pH below 6.0, preferably at a pH between 5.0 and 6.0. The reaction-components should have an osmolality above 150 mosm/kg to further agglutination. The metrological traceability and commutability of results has been proven against different conventional immunoassays employing monoclonal and polyclonal antibodies (but using convential buffers at physiological pH).

The invention claimed is:

1. A method for measuring the presence of calprotectin in a biological sample of a patient by a particle-enhanced turbidimetric immunoassay using a test kit comprising:
    a first aqueous reagent-component comprising:
        20 to 1000 mmol/L organic buffer with a pH in the range from 5.0 to 6.0;
        50 to 300 mmol/L salt of sodium, potassium or lithium;
        0.1 to 1.5% protease-treated serum albumin;
        0.01 to 0.1% (w/v) sodium dodecyl sulfate, and optionally beta-aldoses, triose, tetroses, pentoses, hexoses, glucan, dextran and/or sugar to achieve an osmolality of at least 200 mosmol/kg of $H_2O$; and
    a second reagent-component comprising:
        0.01 to 0.5% (w/v) latex particles of 150 to 350 nm diameter carrying immobilized monoclonal antibodies which bind either one of S100A8 and S100A9 proteins or calprotectin (S100A8/A9);
    the method comprising the steps of:
        a) collecting a predetermined amount of said biological sample;
        b) solubilizing and extracting said biological sample in the first aqueous reagent-component having i) a pH between 5.0 and 6.0, ii) an osmolality of at least 150 mosmol/kg of $H_2O$, iii) wherein the organic buffer is co-coordinating and sequestering calcium and zinc ions, and optionally, homogenizing and extracting the matrix of said biological sample followed by a removal of any particulate material to obtain a sample solution with a solubilized presence of essentially heterodimeric calprotectin (S100A8/A91);
        c) mixing a defined amount of said sample solution of step (b) with an amount of the second reagent-component comprising latex nanoparticles having immobilized two or more monoclonal antibodies or fragments thereof which specifically bind either one of S100A8 and S100A9 or calprotectin (S100A8/A9) to obtain a particle-bound antibody-antigen reaction with calprotectin (S100A8/A9) being present in a defined molecular state;
        d) incubating the mixture of step c) for an interval of time; and
        e) acquiring an optical property of the mixture and determining a signal indicative of the content of calprotectin (S100A8/A9) based on the optical property of the mixture;
        f) relating said content to a calibrated control and assessing the clinical condition of said patient based on the measured presence of calprotectin (S100A8/A9) in said biological sample.

2. The method of claim 1, wherein step e) of acquiring an optical property comprises determining an absorbance, transmittance, reflectance, light scatter, fluorescence, or scintillation value.

3. The method of claim 1, wherein the antibodies are bound to two types of particles having homogenous diameters in the range from i) 150 to 200 nm and ii) from 250 to 350 nm for increased measurement range.

4. The method of claim 1, wherein said particles are carboxylated polystyrene or chloromethyl-activated polystyrene particles.

5. The method of claim 1, wherein the biological sample is faeces or an extract of faeces.

6. The method of claim 1, wherein the buffer composition is made up of at least one salt selected from the group consisting of polycarboxylic acids, tricarboxylic acids, aconitic acids, tricarballylic acids, dicarboxylic acids, oxalic acid, malonic acid, succinic acid, glutaric acid, adipinic acid, pimelinic acid, alpha-, beta-, and gamma-hydroxy carboxylic acids, hydroxy dicarboxylic acids, malic acid, citric acid, tartratic acids, malonic acid, gluconic acid, 5-ketogluconic acid, 2-ketogluconic acid, dihydroxy maleic acid, maleic acid, fumaric acid, nitrilotriacetic acid, lactic acid, and ascorbic acid.

7. The method of claim 1, wherein the particle-bound antibody-antigen reaction is performed in a mixture having a pH between 5.0 and 6.0 and comprising anionic surfactants and Ca2+-coordinated buffer molecules.

8. The method of claim 7, wherein the calcium sequestering buffer of step b) comprises at least one salt of citrate, acetate or maleate, and 0.01 to 0.1 percent by weight of anionic surfactants.

9. The method of claim 1, comprising the addition or presence of unspecific IgM antiserum.

10. The method of claim 1, wherein said biological sample is blood, serum or plasma.

* * * * *